(12) United States Patent
Maeda et al.

(10) Patent No.: US 8,960,685 B2
(45) Date of Patent: Feb. 24, 2015

(54) LAMINATED GASKET

(71) Applicant: Sumitomo Rubber Industries, Ltd., Kobe, Hyogo (JP)

(72) Inventors: Katsushi Maeda, Kobe (JP); Eiji Yao, Kobe (JP)

(73) Assignee: Sumitomo Rubber Industries, Ltd., Kobe (JP)

( * ) Notice: Subject to any disclaimer, the term of this patent is extended or adjusted under 35 U.S.C. 154(b) by 0 days.

(21) Appl. No.: 14/013,798

(22) Filed: Aug. 29, 2013

(65) Prior Publication Data
US 2014/0062036 A1 Mar. 6, 2014

(30) Foreign Application Priority Data
Aug. 30, 2012 (JP) .................................. 2012-190353

(51) Int. Cl.
F16J 15/02 (2006.01)
A61M 5/315 (2006.01)

(52) U.S. Cl.
CPC ............ *F16J 15/02* (2013.01); *A61M 5/31511* (2013.01); *A61M 5/31513* (2013.01); *A61M 2205/0222* (2013.01); *A61M 2205/0238* (2013.01)
USPC ............................ 277/648; 277/650; 277/652

(58) Field of Classification Search
USPC ........................... 277/615, 644, 648, 650, 652
See application file for complete search history.

(56) References Cited

U.S. PATENT DOCUMENTS

| 2,895,773 A | * | 7/1959 | McConnaughey | ............... 92/245 |
| 7,891,528 B2 | * | 2/2011 | Costa et al. | .................... 222/386 |
| 2011/0206577 A1 | * | 8/2011 | Leckebusch | ................... 422/520 |
| 2013/0310772 A1 | * | 11/2013 | Minagawa | ..................... 604/265 |

FOREIGN PATENT DOCUMENTS

| EP | 1020278 A1 | * | 7/2000 |
| JP | 10-314305 A | | 12/1998 |
| JP | 2004-525011 A | | 8/2004 |

* cited by examiner

*Primary Examiner* — Gilbert Lee
(74) *Attorney, Agent, or Firm* — Birch, Stewart, Kolasch & Birch, LLP

(57) ABSTRACT

The present invention provides a gasket for glass or resin syringes which is laminated with an inert resin film and is excellent in plugging properties, liquid-tightness, and slidability. The gasket laminated with an inert resin film has multiple circular ribs that are to be in sliding contact with an inner wall of a syringe barrel, wherein the circular ribs include a front circular rib having a sliding contact portion whose cross section has a diameter that expands substantially linearly toward a back end of the syringe barrel, the linear portion has a length of 10 to 55% of the length of a sliding side face of the gasket, and the diameter of the linear portion which expands substantially linearly toward a back end of the syringe barrel has a diameter expansion ratio X between a minimum diameter r (mm) and a maximum diameter R (mm) of 0.1 to 8.0%.

9 Claims, 3 Drawing Sheets (a)

(b)

(c)

(d)

(e)

(a)

(b)

(c)

(d)

(a)

(b)

(c)

(d)

LAMINATED GASKET

TECHNICAL FIELD

The present invention relates to a gasket laminated with an inert resin film, especially for a prefilled syringe containing a chemical liquid filled therein.

BACKGROUND ART

Prefilled syringes containing a chemical liquid that is previously filled therein are being increasingly used these days because they are very easy to use and can contribute to elimination of misuse. Since such a prefilled syringe includes rubber members that are to be in direct contact with a chemical liquid until use, butyl rubber-based gaskets and nozzle caps, which are excellent in chemical resistance, gas permeation resistance, water vapor permeation resistance and aging resistance, are used for these rubber members in many cases.

Some drugs such as biopharmaceuticals, however, may be affected by interaction with raw rubber of rubber materials, substances extracted from the compounding ingredients, coating agents fallen off the syringe, or the like. In the case of butyl-based rubber members, for example, an oil-type or curable silicone as a lubricant is applied to the inner wall of a syringe barrel and the rubber surfaces of a gasket and nozzle cap for the purpose of improving the slidability of the gasket and preventing firm fixing of the nozzle cap. Thus, such a silicone coating agent, when used with some types of pharmaceuticals, may fall off the inner wall of the barrel or the rubber members and thereby serve as foreign matter, possibly causing a severely harmful influence on the quality of the pharmaceuticals. In particular, the barrel inner wall is coated with a larger amount of silicone coating agent than the gasket. Thus, and in view of the area of contact with the liquid pharmaceutical, the silicone coating agent on the barrel inner wall has a greater influence.

Such a situation has led to development of products made of rubber laminated with, for example, a fluororesin film that has better pharmaceutical stability than butyl rubber. These products are offered for glass syringes or resin prefilled syringes. For example, fluororesin films with excellent chemical resistance are used; in particular, polytetrafluoroethylene (PTFE) with the lowest coefficient of friction is used.

However, a gasket with a fluororesin film laminated on its liquid-contact portion and sliding seal portion contacting with a barrel inner wall, has disadvantageous airtightness and sliding resistance. Especially, skived films have a rough surface and easily suffer poor airtightness between the film and the barrel inner wall. Examples of the factors for deteriorating the airtightness include the smoothness (surface roughness) of a laminated film and the variations of the barrel inner diameter which affect the compression ratio of the gasket when compressed to the barrel inner diameter.

Patent Literature 1 thus proposes a PTFE film produced by a casting method and a UHMWPE film produced by an inflation method; however, these production methods are special and thus impractical. Further, lamination of a PTFE film having a surface roughness Ra of 0.05 μm or lower may suffer a liquid leakage problem. This is because fine irregular marks on the surface of a mold are transferred to the surface of the laminated film and thereby affect the sealability even though the PTFE film is lamination-molded at a molding temperature of 170° C., which is lower than the melting temperature of PTFE (230° C.). The aforementioned variations of the barrel inner diameter are also a serious problem as they affect the compression ratio of the gasket when compressed to the barrel inner diameter. Resin syringes are accurate enough to have an inner diameter tolerance of ±0.1 mm. In contrast, the inner diameter of a tube for glass syringes greatly varies. For example, even a 5-ml or smaller tube has an inner diameter tolerance as large as ±0.15 mm.

Patent Literature 2 proposes a configuration in which the half of a front circular protrusion is laminated. This configuration is formed by a special method in which the unlaminated sliding portion is reduced in diameter to enter inside an upper edge of a punching blade. This method can be applied to small gaskets for 1-ml syringes, for example. However, the method cannot be used to produce large gaskets because the portion which is reduced in diameter to enter inside a punching blade becomes too thick, resulting in difficulty in punching. Further, the upper edge can be shortened by polishing, which causes a maintenance problem.

Meanwhile, a gasket having one or more circular cylindrical ribs is proposed. The arc-shaped circular rib is excellent in terms of sliding resistance but is poor in airtightness because of its small sliding contact area. Many front circular ribs each are designed to have the same diameter to be linear. In this case, the value of sliding resistance increases as the compression ratio, when compressed to the syringe barrel inner diameter, increases. This adversely affects plugging of the gasket. Conversely, if the compression ratio is set to be small, poor airtightness is caused. This is because the front rib portion is made of solid rubber and thus the rubber is difficult to deform.

CITATION LIST

Patent literature

Patent Literature 1: JP H10-314305 A
Patent Literature 2: JP 2004-525011 T

SUMMARY OF INVENTION

Technical Problem

The present invention aims to provide a gasket excellent in liquid-tightness and sliding resistance even though an inert film is lamination-molded thereon.

Solution to Problem

The present invention relates to a gasket, laminated with an inert resin film, which has multiple circular ribs that are to be in sliding contact with an inner wall of a syringe barrel, wherein the multiple circular ribs include a front circular rib having a sliding contact portion whose cross section has a diameter that expands substantially linearly toward a back end of the syringe barrel, the linear portion has a length of 10 to 55% of the length of a sliding side face of the gasket, and the diameter of the linear portion which expands substantially linearly toward the back end of the syringe barrel has a diameter expansion ratio X between a minimum diameter r (mm) and a maximum diameter R (mm) of 0.1 to 8.0%. The diameter expansion ratio X is preferably 0.5 to 7.0%.

The diameter expansion ratio X and the minimum diameter r (mm) of the linear portion preferably satisfy the following formulas (1) and (2):

$$250 \geq r + 30X \qquad (1)$$

and $$40 \leq r + 80X \qquad (2).$$

Preferably, a cavity is formed on top of a screw located at the front circular rib.

The circular rib having the maximum outer diameter at a back end of the linear portion preferably has a compression ratio of 1 to 5% when compressed to the syringe barrel inner diameter.

The inert resin film is preferably a polytetrafluoroethylene (PTFE) film, an ethylene-tetrafluoroethylene copolymer resin (ETFE) film, or an ultra high molecular weight polyethylene (UHMWPE) film.

The inert resin film is preferably 25 to 150 μm in thickness.

The gasket is preferably formed using a gasket mold that is mirror finished so as to allow at least its sliding and sliding contact surfaces to have a center line average roughness Ra of 0.03 μm or lower.

Preferably, a base material of the gasket is a butyl rubber or a thermoplastic elastomer, and has a JIS A hardness of 50 to 70 degrees and a compression set of 20% or lower.

Advantageous Effects of Invention

The gasket of the present invention is laminated with an inert film and has multiple circular ribs that are to be in sliding contact with an inner wall of a syringe barrel. In the gasket, the multiple circular ribs include a front circular rib having a sliding contact portion whose cross section has a diameter that expands substantially linearly toward a back end of the syringe barrel; the linear portion has a length of 10 to 55% of the length of a sliding side face of the gasket; and the diameter of the linear portion expands substantially linearly from the minimum diameter at a predetermined ratio toward the back end of the syringe barrel. Thus, the gasket can be provided as a gasket excellent in liquid-tightness and sliding resistance, by a simple one-step molding process which is excellent in productivity. The present invention also enables to completely avoid the use of lubricative coating agents (e.g. silicone) which are used for the inner walls of syringe barrels and for gaskets, or to reduce the amount of such agents to a very slight amount that has no adverse effect on the quality of pharmaceuticals.

DESCRIPTION OF EMBODIMENTS

The present invention will be described in detail hereinbelow referring to, but not limited to, embodiments.

In the gasket of the present invention which has multiple circular ribs that are to be in sliding contact with the inner wall of a syringe barrel, the front circular rib among the multiple circular ribs has a sliding contact portion whose cross section has a diameter that expands substantially linearly toward the back end of the syringe barrel; the linear portion has a length of 10 to 55% of the length L of the sliding side face of the gasket; and the diameter of the linear portion which expands substantially linearly toward the back end of the syringe barrel has a diameter expansion ratio X between the minimum diameter r (mm) and the maximum diameter R (mm) of 0.1 to 8.0%. FIGS. 1(a) to 1(e) each show a cross-sectional view of an example of the gasket of the present invention. The reference number 1 represents a front circular rib; the reference number 2 represents a circular rib; and the reference number 3 represents a cavity.

Figure 1:
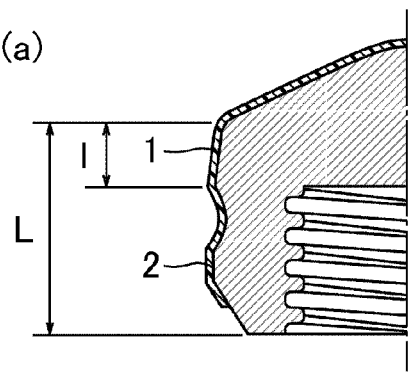
FIG. 1 is cross-sectional views showing examples of the gasket of the present invention having multiple circular ribs that are to be in sliding contact with an inner wall of a syringe barrel.
Figure 1:
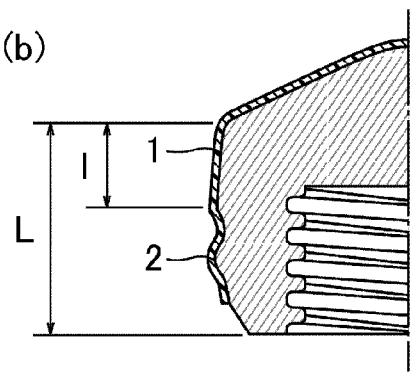
Figure 1:
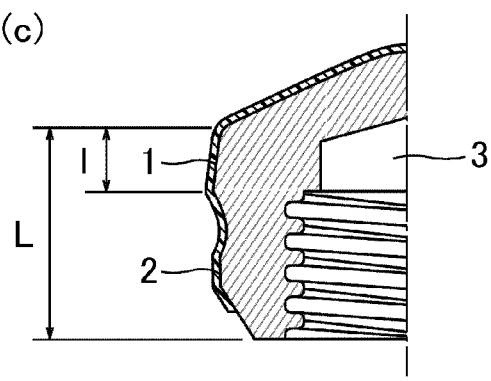
Figure 1:
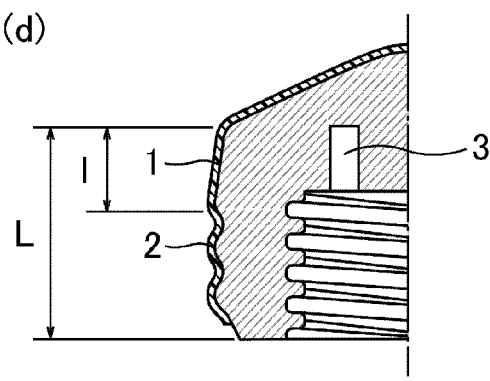
Figure 1:
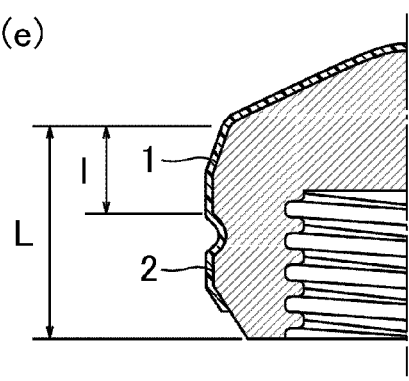
Figure 2:
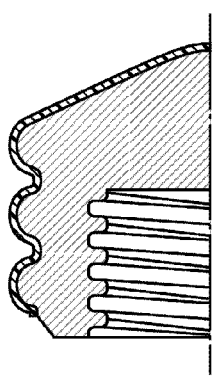
FIG. 2 is cross-sectional views showing examples of conventional gaskets.
Figure 2:
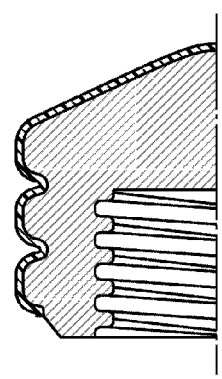
Figure 2:
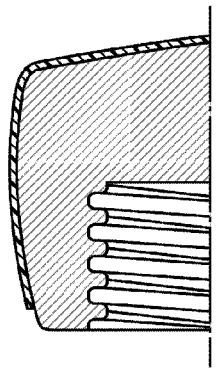
Figure 2:
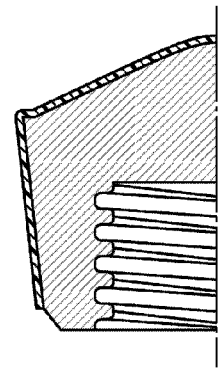

As shown in FIG. 1(a), the length L of the sliding side face is not the length along the side face but the shortest length between the corner of the front circular rib and the back end toward which a rod is to be inserted. The length L does not include the length of a protrusion for preventing adhesion, located at the back end.

The gasket of the present invention has multiple circular ribs that are to be in sliding contact with the inner wall of a syringe barrel. The term "multiple" means two or more, and is not particularly limited as long as the number of ribs is two or more. FIGS. 1(a) to 1(c) and 1(e) show structures with two circular ribs, and FIG. 1(d) shows a structure with three circular ribs.

In comparison with conventional gaskets made only of rubber, film-laminated gaskets are generally difficult to design to simultaneously achieve the following gasket functions: plugging properties (in terms of creases and angled insertion of plug), liquid-tightness, and slidability. In contrast, the gasket of the present invention with a diameter expansion ratio X of 0.1 to 8.0%, in the case of having a circular rib diameter of 5 to 40 mm, can achieve these functions simultaneously by adjusting the length of the substantially linear portion to 1 to 8 mm.

The length of the linear portion is 10 to 55%, preferably 13 to 50%, and more preferably 15 to 45%, of the length L of the sliding side face. The length of the substantially linear portion of the gasket with a circular rib diameter of 5 to 40 mm is preferably 1 to 8 mm, and more preferably 1.5 to 5.0 mm. The length is not the measured length along the sliding surface but the length obtained by projecting the measured line on the center line of the rubber plug, as shown in FIGS. 1(a) to 1(e).

The front circular rib has a sliding contact portion whose cross section has only to be substantially linear, and the whole cross section is not required to be perfectly linear. For example, as shown in FIG. 1(e), the sliding portion may be designed to be substantially linear such that the diameter of the sliding portion on the front end side expands linearly toward the back end of the syringe barrel, while the diameter on the back end side does not expand but is linear. In this case, the length of the linear portion is the sum of the length of the diameter-expanded linear portion and the length of the non-diameter-expanded linear portion.

The starting point of the linear portion of the front circular rib preferably has a diameter varying by at least −3% from the inner diameter of a syringe barrel to be used.

For good design balance of plugging properties, slidability, and liquid leakage resistance, the diameter expansion ratio X is 0.1 to 8.0%, preferably 0.5 to 7.0%.

The more preferred diameter expansion ratio X depends on the syringe size. The ratio X is preferably 0.7 to 8.0%, and more preferably 1.5 to 6.5%, for 1-ml syringes with a barrel inner diameter of about 6 mm; the ratio X is preferably 0.3 to 6.5%, and more preferably 0.7 to 4.5%, for 5-ml syringes with a barrel inner diameter of about 12 mm; and the ratio X is preferably 0.15 to 7.1%, and more preferably 0.5 to 4.5%, for 100-ml syringes with a barrel inner diameter of about 32 mm.

In the gasket of the present invention, the minimum diameter r (mm) of the linear portion and the diameter expansion ratio X (%) between the minimum diameter r (mm) and the maximum diameter R (mm) of the diameter that expands substantially linearly toward the back end of the syringe barrel preferably satisfy the following formulas (1) and (2):

$$250 \geq r+30X \quad (1)$$

and $$40 \leq r+80X \quad (2).$$

The preferred diameter expansion ratio tends to depend on the diameter of the gasket. Thus, a small-diameter gasket needs to have a relatively great diameter expansion ratio, whereas it is sufficient for a large-diameter gasket to have even a relatively small diameter expansion ratio. In other words, the formulas (1) and (2) represent the relation between the diameter and the diameter expansion ratio. The intercept in the formula (1) is 250, and is preferably 180, more preferably 165, and still more preferably 150. The intercept in the formula (2) is 40, and is preferably 60, more preferably 65, and still more preferably 70.

A cavity is preferably formed on top of a screw located at the front circular rib because it allows the maximum-diameter portion of the front circular rib to bend inward, thereby decreasing the sliding resistance. The cavity may have any shape and may be in the form of a cylinder or ring smaller than the minor diameter of the screw portion. The gasket may have one cavity or may have multiple cavities. FIG. 1(c) shows an embodiment with one cavity, and FIG. 1(d) shows an embodiment with a ring cavity.

The circular rib having the maximum diameter preferably has a compression ratio of 1 to 5%, more preferably 2 to 4%, when compressed to the syringe barrel inner diameter. A compression ratio of lower than 1% tends to cause poor liquid-tightness and airtightness. If the compression ratio is higher than 5%, it tends to be difficult to plug the gasket into the barrel, which is likely to cause formation of creases on the film on the circular ribs, resulting in poor liquid-tightness. In addition, the sliding resistance tends to be high. Meanwhile, the circular rib having the minimum diameter preferably has a compression ratio of −3 to 4%, more preferably −1.6 to 3%, when compressed to the syringe barrel inner diameter. A compression ratio of lower than −3% tends to increase the diameter expansion ratio, thereby leading to disadvantageous plugging properties and liquid-tightness. A compression ratio of higher than 4% tends to cause disadvantageous plugging properties and sliding resistance.

The gasket may have one or more circular ribs on the back end side. The diameter of each back-end circular rib preferably varies by ±3%, more preferably ±2%, of the maximum diameter of the front circular rib.

The inert resin film used for molding is preferably 25 to 150 µm, and more preferably 50 to 100 µm, in thickness. A film with a thickness of less than 25 µm tends to be frequently torn upon molding, whereas a film with a thickness of more than 150 µm tends to lead to poor dimension stability of the molded product and to increase the cost, thereby resulting in poor economy.

The resin for the inert resin film is not particularly limited. In order to achieve favorable chemical resistance, the resin is preferably an olefinic resin and/or at least one fluororesin selected from the group consisting of tetrafluoroethylene-ethylene copolymers (ETFE), polytetrafluoroethylene (PTFE), and polychlorotetrafluoroethylene (PCTFE). Containers for medical use can be sterilized by steam sterilization, ethylene oxide gas sterilization, or gamma-ray sterilization. Here, PTFE is less resistant to gamma rays. Thus, ETFE, modified ETFE, and PCTFE are particularly preferred because they are highly resistant to gamma-ray sterilization.

The ETFE is a copolymer of ethylene and tetrafluoroethylene at a mole ratio of 30/70 to 70/30, and it can be copolymerized with another component for the purpose of modification to prepare modified ETFE. Examples of the other components include fluorine-containing olefins and hydrocarbon olefins. Specific examples thereof include a-olefins such as propylene and butene; fluorine-containing olefins such as hexafluoropropylene, vinylidene fluoride, perfluorobutyl ethylene, and trifluorochloroethylene; vinyl ethers such as ethylene vinyl ether, perfluoromethyl vinyl ether, and perfluoropropyl vinyl ether; and fluorine-containing acrylates. About 2 to 10 mol % of these components are copolymerized to modify ETFE.

The modified ETFE may suitably be ETFE containing a functional group that can impart adhesiveness. Examples of such a functional group include a carboxyl group, a carboxylic anhydride group, an epoxy group, a hydroxy group, an isocyanato group, an ester group, an amido group, an aldehyde group, an amino group, a cyano group, a carbon-carbon double bond, a sulfonate group, and an ether group. Examples of products of modified ETFE on the market include Fluon AH-2000 (ASAHI GLASS CO., LTD.).

Examples of the olefinic resin include polyethylenic resins such as polyethylene, ethylene-propylene copolymers, ethylene-propylene-non-conjugated diene copolymers, ethylene-butene copolymers, ethylene-hexene copolymers, ethylene-octene copolymers, ethylene-vinyl acetate copolymers, ethylene-vinyl alcohol copolymers, ethylene-ethyl acrylate copolymers, and chlorinated polyethylene; polypropylenic resins such as polypropylene, propylene-ethylene random copolymers, propylene-ethylene block copolymers, and chlorinated polypropylene; and polybutene, polyisobutylene, polymethylpentene, and copolymers of cyclic olefins. Polyethylene (especially, ultra high molecular weight polyethylene (UHMWPE)) is preferred. These olefinic resins may contain fluorine.

The inert film is preferably subjected to a treatment to enhance adhesion to rubber or the like. Examples of such a treatment to enhance adhesion include chemical treatments, treatments for roughing the surface of a film, and combinations thereof. Specific examples thereof include sodium treatment, glow discharge treatment, plasma treatment (discharge treatment) under the atmospheric pressure or in vacuum, excimer laser treatment (discharge treatment), and ion beam treatment.

The base material of the gasket may be any elastic material. Examples of the elastic material include various rubber materials such as natural rubber, butyl rubber, isoprene rubber, butadiene rubber, styrene-butadiene rubber, silicone rubber, epichlorohydrin rubber, ethylene-propylene rubber, and nitrile rubber; and various thermoplastic elastomers such as polyurethane elastomers, polyester elastomers, polyamide elastomers, olefinic elastomers, and styrenic elastomers. These elastic materials may be used alone or as a blend of multiple materials. Particularly preferred are materials that acquire elasticity by vulcanization. In the case of vulcanizable materials, compounding ingredients known in the rubber industry, such as vulcanizing agents (e.g. sulfur) and vulcanization accelerators, may be appropriately added.

The JIS A hardness of the base material of the gasket is not particularly limited. It is preferably 50 to 70 degrees, and more preferably 55 to 65 degrees. A JIS A hardness of lower than 50 degrees may cause leakage due to deformation of the gasket during sliding, and may cause removal of the plunger rod from the gasket during suction. A JIS A hardness of higher than 70 degrees tends to require a higher molding pressure which is likely to cause the film to be torn easily, and to make it difficult to demold the gasket.

The compression set is also not particularly limited. It is preferably 20% or lower, and more preferably 15% or lower. A compression set of higher than 20% tends to cause circular ribs to be reduced in diameter during plugging, sterilization, and storage so that the compression ratio becomes insufficient, thereby failing to maintain the liquid-tightness and airtightness between the gasket and the barrel inner wall.

The compression set herein means a value measured at 25% compression and 70±1° C. for 22 hours.

The gasket of the present invention can be obtained as follows. The compounding materials are kneaded at a predetermined compounding ratio using an internal mixer, an open roll mill or the like to prepare a kneaded mixture. This kneaded mixture is formed into an unvulcanized rubber sheet using a calender or sheet forming machine. Then the unvulcanized rubber sheet with predetermined weight and size and an inert film are stacked on a mold, and then molded using a vacuum press to yield a molded sheet for the laminated gasket.

The molding conditions are not particularly limited and may be appropriately set. The molding temperature is preferably 155° C. to 200° C., and more preferably 165° C. to 180° C. The molding time is preferably 1 to 20 minutes, more preferably 3 to 15 minutes, and still more preferably 5 to 10 minutes.

The part of the mold to be used which forms a sliding surface is preferably mirror finished so as to have a smooth surface having an arithmetic mean roughness Ra of 0.03 μm or lower as measured at a cutoff value of the part of 0.08 mm. Such a mold can provide as the molded product a lamination-molded rubber member having a lower surface roughness than that of the original film. The value Ra is preferably 0.02 μm or lower, and more preferably 0.015 μm or lower. The arithmetic mean roughness (Ra) in the present invention can be measured in accordance with JIS B0601-2001.

Unnecessary portions are then cut and removed from the molded gasket, and is subsequently washed, sterilized, dried, and checked for its appearance to prepare a completed gasket.

EXAMPLES

The present invention will be described in detail hereinbelow referring to, but not limited to, examples.

The specification of the fluororesin film used in the examples is mentioned below.
Inert Resin Film
Modified PTFE skived film: trade name "NEW VALFLON" (NIPPON VALQUA INDUSTRIES, LTD., film thickness: 70 μm, center line average surface roughness: 0.11 μm)
Gasket Base Material
Chlorinated butyl rubber material (JIS A hardness: 58 degrees, compression set: 14%)

Examples 1 to 9 and Comparative Examples 1 to 7

A PTFE film (prepared by skiving, thickness: 70 μm, one surface was adhesion-treated) was stacked on an unvulcanized rubber sheet made from chlorinated butyl rubber, and the stack was placed on a mold and then molded and vulcanization-bonded using a vacuum press at 175° C. for 10 minutes. The obtained gasket was subjected to the following tests. The diameter of the circular rib on the back end side of the gasket varied by 0.5 to 1.5% of the maximum diameter of the front circular rib.

For a 1-ml COP-resin syringe, the inner diameter of the barrel was 6.35 mm and the length of the sliding portion was 7.0 mm; for a 5-ml COP-resin syringe, the inner diameter of the barrel was 12.45 mm and the length of the sliding portion was 9.5 mm; and for a 100-ml COP-resin syringe, the inner diameter of the barrel was 32.06 mm and the length of the sliding portion was 14.0 mm.

(Gasket Plugging Properties)

A jig with a certain length was fit into the screw portion of the gasket, and the gasket in this state was placed with the liquid-contact side facing up. Then the gasket was inserted straight into a syringe barrel so that the gasket was plugged. Next, water colored by methylene blue was filled through a nozzle into the syringe and left for 15 hours. Whether the front circular rib was inserted at an angle into the barrel was visually observed. Whether crease(s) are formed on the front circular rib was observed at a magnification of 10×. For the 1-ml and 5-ml syringes, the test was performed with n=20 for evaluation. For the 100-ml syringe, the test was performed with n=10 for evaluation.

Good: The angled insertion of plug and/or the formation of creases were observed with an incidence of 10% or less.

Acceptable: The angled insertion of plug and/or the formation of creases were observed with an incidence of 10 to 30%.

Poor: The angled insertion of plug and/or the formation of creases were observed with an incidence of 30% or more.

(Sliding Resistance)

The syringe was equipped with a plunger rod and a needle. Then, the liquid was ejected at a speed of 100 mm/min with an autograph until the gasket reached a position 10% of the maximum capacity. During this movement, the average value was determined. The test was performed with n=10, and the sliding resistance was evaluated based on the following criteria.

TABLE 1

| Evaluation | 1 ml<br>Needle 23G | 5 ml<br>Needle 23G | 100 ml<br>Needle 18G |
|---|---|---|---|
| Good | Smoothly move at 8N or lower without knocking | Smoothly move at 10N or lower without knocking | Smoothly move at 40N or lower without knocking |
| Acceptable | Move at 12N or lower | Move at 15N or lower | Move at 50N or lower |
| Poor | Move at 12N or higher | Move at 15N or higher | Move at 50N or higher |

(Liquid Leakage)

This test is performed in conformity with the Notification "Mekkin-zumi chusha-tou kijun (standards for sterile injection syringes)" issued on Dec. 11, 1998, Iyakuhatsu No. 1079 by the Director of the Pharmaceutical and Medical Safety Bureau, the Ministry of Health, Labour and Welfare.

The gasket samples with the respective sizes, nozzle caps, 5-ml barrels, and plungers were prepared. A jig longer than the screw was fit into the screw portion of each gasket, and the gasket in this state was placed with the liquid-contact side facing up. Then the gasket was inserted straight into the syringe barrel so that the gasket was plugged. Next, water colored by methylene blue was filled through the nozzle into the syringe to a graduation line corresponding to ¾ of the nominal capacity. Then, the nozzle cap and the plunger were attached. The syringe was faced down and a predetermined pressure (1-ml syringe: 490 kPa, 5-ml syringe: 343 kPa, 100-ml syringe: 196 kPa) was applied to the plunger for 10 seconds. After the syringe was left for one day, the syringe was observed at a magnification of 10× for the presence of leakage into the valley portion (between the front circular rib and the back-end circular rib) of the gasket. This test was performed with n=20 for the 1-ml and 5-ml syringes, and with n=10 for the 100-ml syringe for evaluation.

Good: No leakage was observed.
Acceptable: Slight linear leakage was observed.
Poor: Leakage was clearly observed.
Tables 2 to 4 show the evaluation results.

The ratio (%) of the length of the rib, the diameter expansion ratio X (%) of the front rib, and the compression ratio (%) in the tables were calculated as follows using the values in Example 1 as examples.

Ratio(%) of length of rib=(length of front circular rib)/(length of sliding portion)×100=4.0/9.5× 100=42(%)

Diameter expansion ratio X(%) of front rib={(maximum diameter)−(minimum diameter)}/(minimum diameter)×100=(12.85−12.75)/12.75× 100=0.78(%)

Compression ratio(%) of maximum diameter={(maximum diameter of circular rib)−(barrel inner diameter)}/(maximum diameter of circular rib)× 100=(12.85−12.45)/12.85×100=3.11(%)

Compression ratio(%) of minimum diameter={(minimum diameter of circular rib)−(barrel inner diameter)}/(minimum diameter of circular rib)× 100=(12.75−12.45)/12.75×100=2.35(%)

TABLE 2

Figure 3:
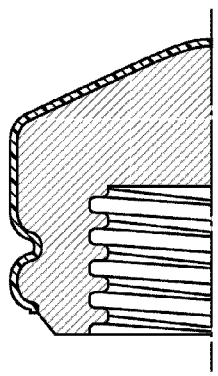
FIG. 3 is cross-sectional views showing other examples of conventional gaskets.
Figure 3:
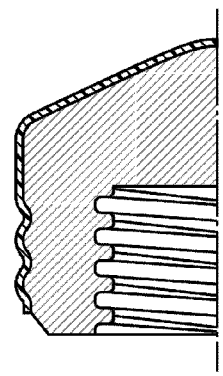
Figure 3:
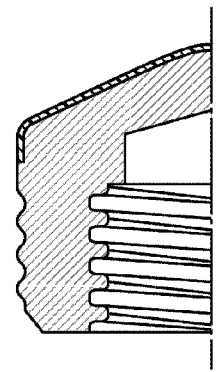
Figure 3:
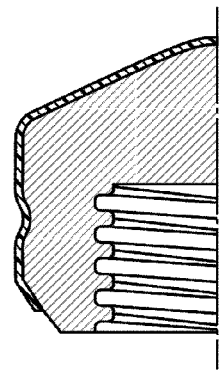

| Number of Example | | Example 1 | Example 2 | Example 3 | Example 4 | Comparative Example 1 | Comparative Example 2 | Comparative Example 3 |
|---|---|---|---|---|---|---|---|---|
| Configuration of gasket (5 ml, barrel inner diameter: 12.45 mm) | Shape of front rib | FIG. 1(a) | FIG. 1(a) | FIG. 1(e) | FIG. 1(b) | FIG. 3(a) | FIG. 3(b) | FIG. 1(a) |
| | Minimum diameter r (mm) of linear portion | 12.75 | 12.45 | 12.30 | 12.75 | 12.80 | 12.85 | 11.85 |
| | Maximum diameter R (mm) of linear portion | 12.85 | 12.85 | 12.85 | 12.85 | 12.80 | 12.85 | 12.85 |
| | Length of rib — Shape | Tapered | Tapered | Tapered/straight | Tapered | Straight | Straight | Tapered |
| | Length (mm) | 4.0 | 4.0 | 2.5/2.5* | 4.0 | 4.0 | 4.0 | 4.0 |
| | Ratio (%) | 42 | 42 | 26/26 | 42 | 42 | 42 | 42 |
| | Diameter expansion ratio X (%) of front rib | 0.78 | 3.21 | 4.47 | 0.78 | 0 | 0 | 8.44 |
| | r + 30X | 36 | 109 | 146 | 36 | 13 | 13 | 265 |
| | r + 80X | 75 | 269 | 370 | 75 | 13 | 13 | 687 |
| | Compression ratio (%) of minimum diameter | 2.35 | 0 | −1.22 | 2.35 | 2.73 | 3.11 | −5.06 |
| | Compression ratio (%) of maximum diameter | 3.11 | 3.11 | 3.11 | 3.11 | 2.73 | 3.11 | 3.11 |
| Evaluation of properties | Gasket plugging properties | Good | Good | Good | Good | Acceptable | Poor | Acceptable |
| | Sliding resistance (N) | Good to Acceptable | Good to Acceptable | Good | Good | Good to Acceptable | Acceptable to poor | Good |
| | | 7 to 12 | 7 to 11 | 6 to 10 | 7 to 9 | 9 to 14 | 11 to 19 | 7 to 10 |
| | Liquid leakage — Good | 20/20 | 18/20 | 20/20 | 20/20 | 15/20 | 14/20 | 15/20 |
| | Acceptable | 0/20 | 2/20 | 0/20 | 0/20 | 4/20 | 6/20 | 5/20 |
| | Poor | 0/20 | 0/20 | 0/20 | 0/20 | 1/20 | 0/20 | 0/20 |

*Length of tapered portion/length of straight portion

TABLE 3

| | | Number of Example | | | |
|---|---|---|---|---|---|
| | | Example 5 | Example 6 | Comparative Example 4 | Comparative Example 5 |
| Configuration of gasket (1 ml, barrel inner diameter: 6.35 mm) | Shape of front rib | FIG. 1(a) | FIG. 1(a) | FIG. 3(a) | FIG. 1(a) |
| | Minimum diameter r (mm) of linear portion | 6.35 | 6.60 | 6.65 | 6.10 |
| | Maximum diameter R (mm) of linear portion | 6.65 | 6.65 | 6.65 | 6.70 |
| | Length of rib — Shape | Tapered | Tapered | Straight | Tapered |
| | Length (mm) | 3.0 | 2.5 | 2.5 | 4.0 |
| | Ratio (%) | 43 | 36 | 36 | 57 |
| | Diameter expansion ratio X (%) of front rib | 4.72 | 0.76 | 0 | 9.84 |
| | r + 30X | 148 | 29 | 7 | 301 |
| | r + 80X | 384 | 67 | 7 | 793 |
| | Compression ratio (%) of minimum diameter | 0 | 3.79 | 4.51 | −4.1 |
| | Compression ratio (%) of maximum diameter | 4.51 | 4.51 | 4.51 | 5.22 |
| Evaluation of properties | Gasket plugging properties | Good | Good | Poor | Poor |
| | Sliding resistance (N) | Good | Good to Acceptable | Acceptable to poor | Acceptable to poor |
| | | 5 to 8 | 6 to 10 | 10 to 16 | 11 to 15 |
| | Liquid leakage — Good | 19/20 | 20/20 | 5/20 | 14/20 |
| | Acceptable | 1/20 | 0/20 | 10/20 | 6/20 |
| | Poor | 0/20 | 0/20 | 5/20 | 0/20 |

TABLE 4

| Number of Example | | Example 7 | Example 8 | Example 9 | Comparative Example 6 | Comparative Example 7 |
|---|---|---|---|---|---|---|
| Configuration of gasket (100 ml, barrel inner diameter: 32.06 mm) | Shape of front rib | FIG. 1(a) | FIG. 1(a) | FIG. 1(e) | FIG. 3(a) | FIG. 1(a) |
| | Minimum diameter r (mm) of linear portion | 32.36 | 33.00 | 33.00 | 33.30 | 30.60 |
| | Maximum diameter R (mm) of linear portion | 33.36 | 33.40 | 33.26 | 33.30 | 33.40 |
| | Length of rib — Shape | Tapered | Tapered | Tapered/straight | Straight | Tapered |
| | Length (mm) | 6 | 6 | 2.5/3.0* | 5 | 8 |
| | Ratio (%) | 43 | 43 | 18/21 | 36 | 57 |
| | Diameter expansion ratio X (%) of front rib | 3.09 | 1.21 | 0.79 | 0 | 9.15 |
| | r + 30X | 125 | 69 | 57 | 33 | 305 |
| | r + 80X | 280 | 130 | 96 | 33 | 763 |
| | Compression ratio (%) of minimum diameter | 0.93 | 2.85 | 2.85 | 3.72 | −4.77 |
| | Compression ratio (%) of maximum diameter | 3.9 | 4.01 | 3.61 | 3.72 | 4.01 |
| Evaluation of properties | Gasket plugging properties | Good | Good | Good | Poor | Poor |
| | Sliding resistance (N) | Good | Good to Acceptable | Acceptable | Poor | Acceptable to poor |
| | | 33 to 39 | 35 to 44 | 41 to 48 | 50 to 66 | 46 to 60 |
| | Liquid leakage — Good | 9/10 | 10/10 | 10/10 | 6/10 | 5/10 |
| | Acceptable | 1/10 | 0/10 | 0/10 | 2/10 | 5/10 |
| | Poor | 0/10 | 0/10 | 0/10 | 2/10 | 0/10 |

*Length of tapered portion/length of straight portion

The gaskets in Comparative Examples 1 to 7 (conventional gaskets) are particularly poor in plugging properties, thereby affecting slidability and liquid leakage. In the gaskets of the present invention, in contrast, the front circular rib has a sliding contact portion whose cross section is substantially linear; the linear portion has a length of 10 to 55% of the whole length of the gasket; and the diameter of the linear portion expands substantially linearly from the minimum diameter at a predetermined ratio toward the back end of the syringe barrel. Therefore, as shown in Examples 1 to 9, the gaskets are excellent in terms of all the properties, gasket plugging properties, sliding resistance, and liquid leakage.

REFERENCE SIGNS LIST

1: front circular rib
2: circular rib
3: cavity
L: length of sliding side face
l: length of sliding contact portion of front circular rib

The invention claimed is:

1. A gasket, laminated with an inert resin film, which has multiple circular ribs that are to be in sliding contact with an inner wall of a syringe barrel, wherein the multiple circular ribs include a front circular rib having a sliding contact portion whose cross section has a diameter that expands substantially linearly toward a back end of the syringe barrel, the linear portion has a length of 10 to 55% of the length of a sliding side face of the gasket, and the diameter of the linear portion which expands substantially linearly toward the back end of the syringe barrel has a diameter expansion ratio X between a minimum diameter r (mm) and a maximum diameter R (mm) of 0.1 to 8.0%.

2. The gasket according to claim 1, wherein the diameter expansion ratio X is 0.5 to 7.0%.

3. The gasket according to claim 1, wherein the diameter expansion ratio X and the minimum diameter r (mm) of the linear portion satisfy the following formulas (1) and (2):

$$250 \geq r + 30X \quad (1)$$

and $$40r + 80X \quad (2).$$

4. The gasket according to claim 1, wherein a cavity is formed on top of a screw located at the front circular rib.

5. The gasket according to claim 1, wherein the circular rib having the maximum outer diameter at a back end of the linear portion has a compression ratio of 1 to 5% when compressed to the syringe barrel inner diameter.

6. The gasket according to claim 1, wherein the inert resin film is a polytetrafluoroethylene film, an ethylene-tetrafluoroethylene copolymer resin film, or an ultra high molecular weight polyethylene film.

7. The gasket according to claim 1, wherein the inert resin film is 25 to 150 μm in thickness.

8. The gasket according to claim 1, which is formed using a gasket mold that is mirror-finished so as to allow at least its sliding and sliding contact surfaces to have a center line average roughness Ra of 0.03 μm or lower.

9. The gasket according to claim 1, wherein a base material of the gasket is a butyl rubber or a thermoplastic elastomer, and has a JIS A hardness of 50 to 70 degrees and a compression set of 20% or lower.

* * * * *